United States Patent [19]

Kohno et al.

[11] Patent Number: 4,831,274
[45] Date of Patent: May 16, 1989

[54] SURFACE INSPECTING DEVICE FOR DETECTING THE POSITION OF FOREIGN MATTER ON A SUBSTRATE

[75] Inventors: Michio Kohno; Akiyoshi Suzuki, both of Tokyo, Japan

[73] Assignee: Canon Kabushiki Kaisha, Tokyo, Japan

[21] Appl. No.: 76,619

[22] Filed: Jul. 23, 1987

[30] Foreign Application Priority Data

Jul. 28, 1986 [JP] Japan ................. 61-175686

[51] Int. Cl.⁴ .......................................... G01N 21/88
[52] U.S. Cl. ..................................... 250/563; 250/572
[58] Field of Search .............. 250/572, 571, 562, 563, 250/559, 561; 356/429, 430, 431

[56] References Cited

U.S. PATENT DOCUMENTS 4,218,142 8/1980 Kryger et al. ............... 250/572
4,247,204 1/1981 Merlen et al. ............... 250/572
4,468,120 8/1984 Tanimoto et al. ............ 250/572
4,547,895 10/1985 Mita et al. ................... 250/572

Primary Examiner—David C. Nelms
Attorney, Agent, or Firm—Fitzpatrick, Cella, Harper & Scinto

[57] ABSTRACT

A surface inspecting device may be used to inspect the surface of a reticle having a central transparent portion, bearing a circuit pattern to be photoprinted on a semiconductor wafer, and a peripheral light-intercepting portion surrounding the central transparent portion. Particularly, the device is usable to inspect the presence/absence of dust or foreign particles which are adhered to the transparent portion of the reticle. The device is arranged to detect the position of such a foreign particle, if any, adhered to the transparent portion, while taking as a reference the boundary between the transparent portion and the light-intercepting portion of the reticle. This operation permits accurate detection of the position of the particle on the transparent portion of the reticle.

4 Claims, 7 Drawing Sheets

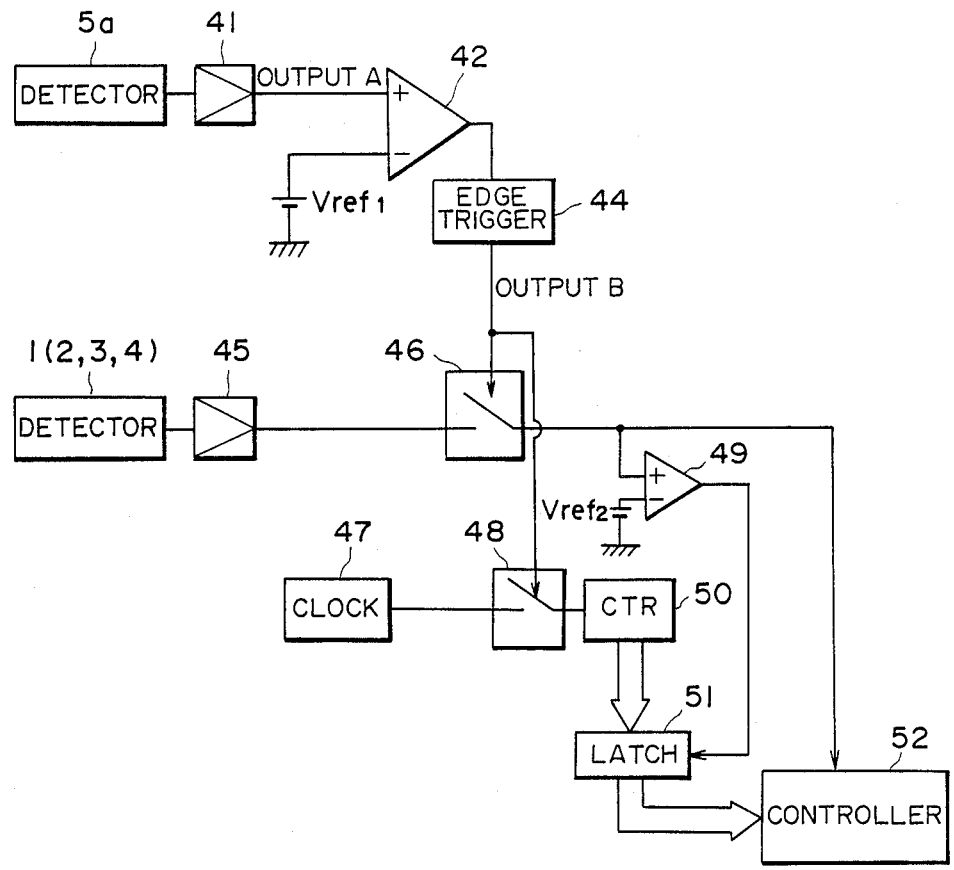
F I G. 4

SURFACE INSPECTING DEVICE FOR DETECTING THE POSITION OF FOREIGN MATTER ON A SUBSTRATE

FIELD OF THE INVENTION AND RELATED ART

This invention relates generally to a surface inspecting device for inspecting the state of the surface of an article. More particularly, the invention is concerned with a surface inspecting device, suitably usable in the field of manufacture of semiconductor devices such as integrated circuits, for inspecting the surface of a transparent substrate such as a reticle having a circuit pattern formed thereon and for detecting the presence/absence of any disfigurement of the circuit pattern or array and any foreign particle or particles such as, for example, non-transparent dust, adhered to the surface of the substrate.

For the manufacture of semiconductor devices such as integrated circuits, usually reticles each comprising a transparent substrate and having a pattern, prepared on the substrate surface for the manufacture of microcircuits, are used. These reticles are used with an alignment and exposure apparatus, called a "stepper" or "mask aligner", so that the microcircuits manufacturing pattern (hereinafter "circuit pattern", of the reticle is transferred onto or photoprinted upon the surface of a wafer whose surface is coated with a photosensitive or resist material. If any disfigurement of the pattern or any foreign particle or particles such as dust, other than the circuit pattern, are existing on the surface of the substrate, also they are photoprinted upon the wafer at the time of the pattern transfer. This decreases the yield of microcircuits.

Particularly, in a case where a step-and-repeat type exposure apparatus is used so as to photoprint the same circuit pattern of a reticle upon each of different shot areas on a wafer in a step-and-repeat manner, only a single foreign particle on the reticle is sufficient to critically damage or decrease the yield of microcircuits because such foreign particle is photoprinted upon every shot area on the wafer.

In consideration of this, the microcircuit manufacturing processes include inspection of the surface of each reticle so as to detect the existence/absence of any foreign particle or particles on the surface being examined.

For the surface inspection, it may be desirable to discriminate such foreign particle that is existing in a central region (pattern bearing region) of a reticle from such foreign particle that is existing in a peripheral region of the reticle, outside the pattern bearing region, since the former often critically damages the manufactured circuit device whereas the latter does not damage the circuit device. Namely, it may be desirable to discriminate the location of each foreign particle in the coordinate system concerning the reticle surface.

Also, it may be important to precisely detect the position itself of each particle existing in the pattern bearing region of the reticle. This is because, of the foreign particles adhered to the pattern bearing region of the reticle surface, such particle that is existing just upon a portion, such as a chromium-coated portion or a pattern-element portion, which has a light-intercepting property with respect to the light used for the photoprinting, does not substantively affect the photoprinting of the circuit pattern. If all the foreign particles adhered to the reticle surface are existing on such portion, it may be possible to omit a cleaning process for cleaning the reticle after it is extracted out of the inspecting device. The omission of the cleaning process is very desirable in respect to the simplicity of the manufacturing process.

While many proposals have been made of the surface inspection, no one has achieved detection of the position of a foreign particle adhered to the surface being examined. Almost all the prior art surface inspecting devices employ a light beam scanning method for the inspection of the surface to be examined. However, in these devices, it is not possible to detect the position being scanned by the light beam (i.e. the position on which the light beam is incident at a moment). At the best, the position of the center of the circuit pattern may be calculated with a low degree of accuracy on the basis of, e.g., the angle of rotation of a mirror which is provided to scanningly deflect the light beam. According to this technique, however, the accuracy of detecting the position of the inspecting point on the reticle at a moment is affected by the accuracy of supporting the reticle by a reticle support of the inspecting device, any positional deviation between the center of the circuit pattern of the reticle and the center of the reticle as determined by the configuration thereof, and so on. Therefore, it is very difficult to determine the exact position of the inspecting point on the reticle at each moment during the inspection.

SUMMARY OF THE INVENTION

It is accordingly a primary object of the present invention to mitigate the inconveniences described hereinbefore and to provide a surface inspecting device for inspecting the surface of a substrate such as a reticle, by which apparatus the position of a foreign particle such as dust adhered to the substrate, if any, or any disfigurement such as a scratch on the substrate can be detected very accurately. Such detection is not adversely affected by the substrate supporting accuracy of the device or the deviation of the center of the surface of the substrate to be examined.

Briefly, in accordance with one preferred form of the present invention, to achieve the above object, there is provided a surface inspecting device wherein a patterned surface of a substrate, having a transparency, is scanned with a light beam such that, by detecting a reflectively scattered or transmissively scattered light from the substrate, the state of the patterned surface of the substrate, e.g. the presence/absence of any foreign particle on the substrate as well as the position of the particle, is examined. The inspecting device is provided with photoelectric means for receiving the scanning light as reflected from and/or passed through a portion of the substrate in the neighborhood of a boundary between a transparent region of the substrate and a peripheral light-intercepting region surrounding the transparent region. On the basis of an output from the photoelectric means and of information concerning the scan position, the position of the point of inspection, at each moment, upon the surface of the substrate can be determined.

In the surface inspecting device according to an embodiment of the present invention, when the scanning beam scans the portion of the substrate at the boundary between the transparent region and the peripheral light-intercepting region, the reflected or transmitted light from such portion changes quickly. This change is detected by the photoelectric means, whereby the scan position can be determined exactly. Also, the transparent substrate, particularly where it is a reticle, has its boundary between the transparent region and the peripheral light-intercepting region formed very precisely. Thus, by determining the boundary at the time of optical scanning, the range of the transparent region as well as the range of the peripheral light-intercepting region can be determined very accurately. Additionally, the position of a foreign particle or a scratch, if any, can be determined very accurately, while taking the position of the boundary as a reference.

These and other objects, features and advantages of the present invention will become more apparent upon a consideration of the following description of the preferred embodiments of the present invention taken in conjunction with the accompanying drawings

BRIEF DESCRIPTION OF THE DRAWINGS

FIG. 4 is a block diagram of a position detecting system included in the first embodiment.

DESCRIPTION OF THE PREFERRED EMBODIMENTS

Figure 1:
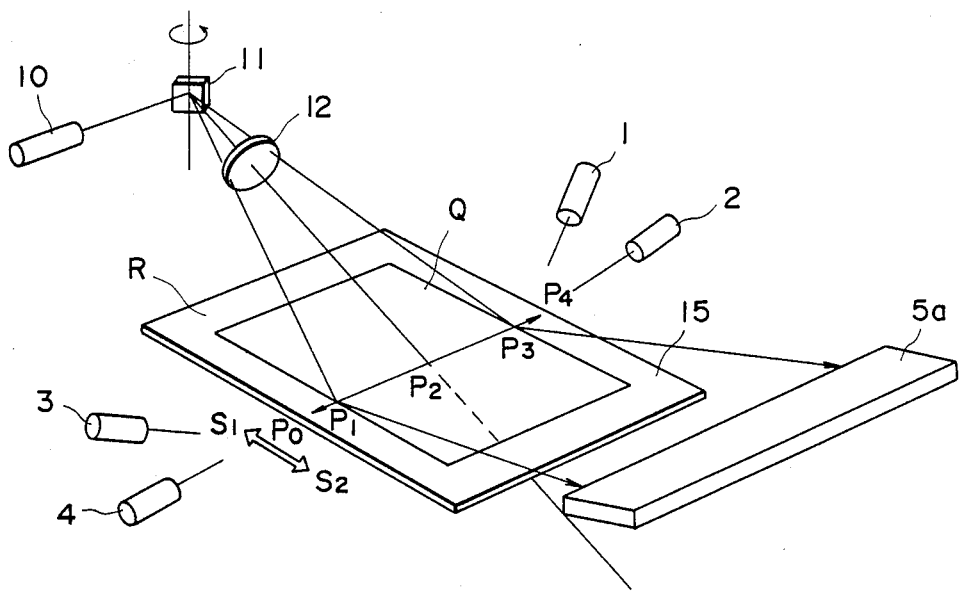
FIG. 1 is a perspective view schematically showing an optical arrangement of a surface inspecting device according to a first embodiment of the present invention.

Referring first to FIG. 1, there is shown a surface inspecting device according to a first embodiment of the present invention. In the arrangement shown in FIG. 1, a light beam emitted from a laser 10 is scanningly deflected by a rotatable or oscillation type scanning mirror 11 so that, with the aid of a lens 12, the light beam scans the surface of a reticle 15 (an article to be examined) in a direction from a point P0 via points P1, P2 and P3 to a point P4. In synchronism with the scan of the reticle 15 surface, a reticle stage, not shown, supporting the reticle 15 is moved in a direction from S1 to S2. By repeatedly scanning the reticle 15 surface while moving the reticle, the whole surface of the reticle can be inspected. If a foreign particle adhered to the reticle 15 surface is irradiated with the scanning beam, the particle scatters the light and the scattered light is received by a suitable photoelectric detecting means such as, for example, photodetectors 1-4 as illustrated in FIG. 1.

Thus, a particle detection signal is obtained. While there are many varieties of processes for detecting such a foreign particle or discriminating such a foreign particle from a circuit pattern, essentially the present invention is applicable to all of these processes with the same advantageous effects.

Figure 9:
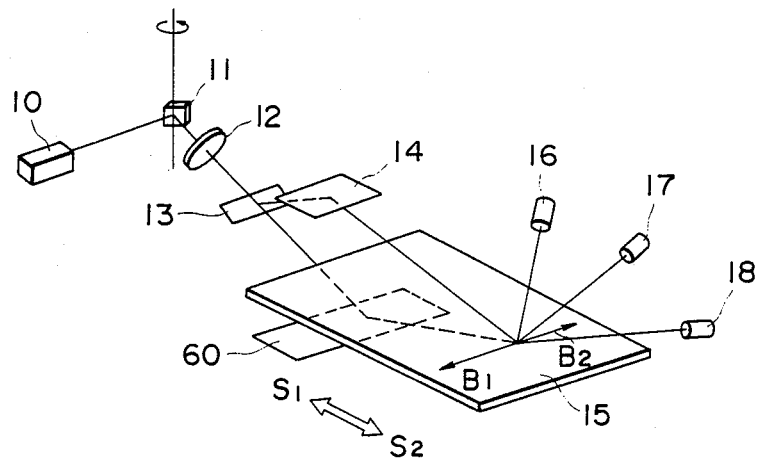
FIGS. 9 and 10 are perspective views, respectively, showing optical arrangements to which the present invention is applicable.
Figure 10:
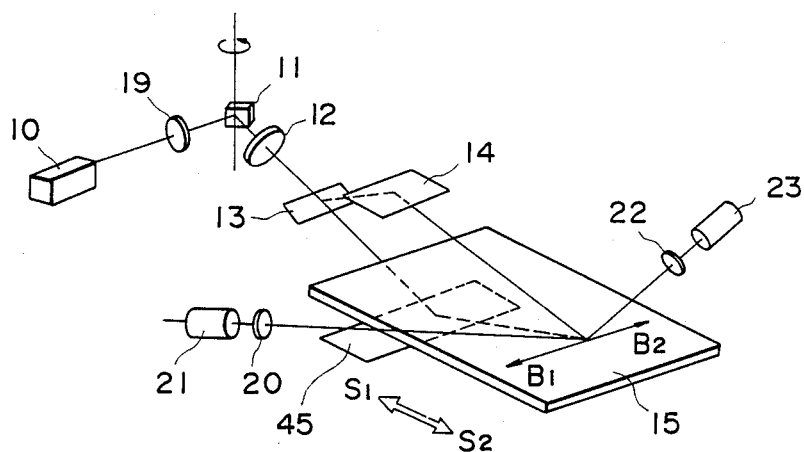

Examples of the manner of discriminating a foreign particle from a circuit pattern are illustrated in FIGS. 9 and 10. Of these examples, the FIG. 9 example is a case which utilizes a phenomenon that a foreign particle scatters the light substantially in all directions. In the FIG. 9 case, a light beam from a laser 10 is projected by means of a scanning mirror 11 and a lens 12 upon upper and lower surfaces of a substrate such as a reticle 15 in sequence. For this purpose, a retractable mirror 13 which is selectively cooperable with one of mirrors 14 and 60 is used. The mirror 13 is movable so as to be inserted into or retracted out of the path of the light from the lens 12 so as to selectively define, with the cooperation with the mirror 14 or 60, one of an optical path directed to the upper surface of the reticle and an optical path directed to the lower surface of the reticle. The scanning mirror 11 is rotated or oscillated so that the reticle 15 surface is scanned with the light from the laser 10. There are provided a plurality of light-receiving elements 16, 17 and 18 which are disposed at positions remote from an optical path of the light directly reflected from the substrate 15 and an optical path of the light directly transmitted by the substrate 15. Namely, the light-receiving elements 16–18 are disposed so as to detect only the scattered lights from the substrate 15. Thus, by using output signals from the light-receiving elements 16–18, the presence/absence of any foreign particle adhered to the substrate 15 surface is detected More specifically, when light is projected upon a circuit pattern, it is diffracted by edges of the circuit pattern with a specific and strong directivity which depends on the orientation of the edges of the circuit pattern. Therefore, the light-receiving elements 66–18 produce signals of different output levels. On the other hand, when a light impinges upon a foreign particle, it is scattered substantially in all directions. As a result, the light-receiving elements 16–18 produce signals of substantially the same output levels. Accordingly, by comparing the output signals of the light-receiving elements 16–18, the presence of such a foreign particle can be detected.

The example of FIG. 10 is a case which utilizes a phenomenon that, when polarized light impinges upon a foreign particle, the state of polarization of the light is disturbed by the particle. In the optical arrangement of FIG. 10, a light beam from a laser 10 enters into a polarizer 19 whereby it is converted into a polarized light having a predetermined state of polarization. The polarized light from the polarizer 19 is projected by means of a scanning mirror 11 and a lens 12 and with the selective cooperation of mirrors 13, 14 and 45 upon the upper and lower surfaces of a substrate 15 in sequence. The mirror 13 is similarly retractable, as the mirror 13 of the FIG. 9 example. By rotating or oscillating the scanning mirror 11, the substrate 15 surface is scanned with the scanningly deflected light. In this example, there are provided two light-receiving elements 21 and 23 which are disposed at positions remote from an optical path of the light directly reflected from the substrate 15 and an optical path of the light directly transmitted by the substrate 15. Further, in this example, there are provided two analyzers 20 and 22 each disposed in front of an associated one of the two light-receiving elements 21 and 23. By detecting, with the two light-receiving elements 21 and 23, the difference in the quantity of reception of light which results from the difference in the ratio of polarization components, between the light diffracted by the circuit pattern and the light scattered by the foreign particle, the circuit pattern and the foreign particle on the substrate 15 surface are detected.

Figure 2:
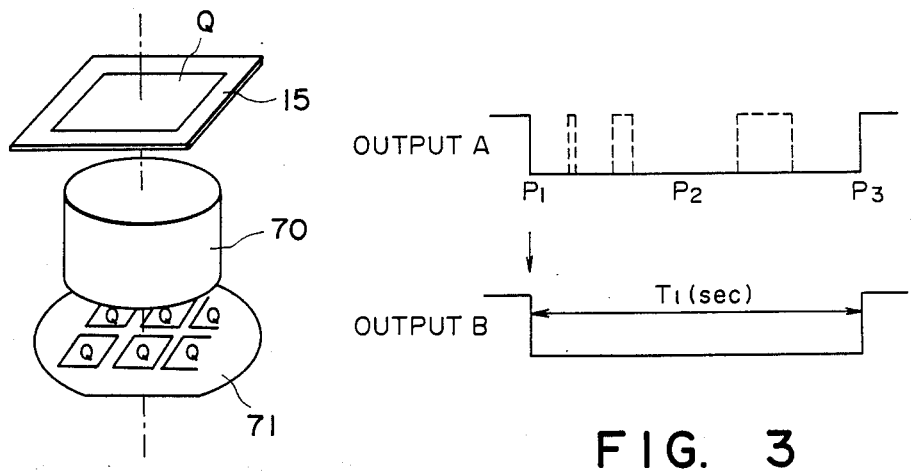
FIG. 2 is a representation showing a fundamental arrangement of a step-and-repeat type projection exposure system.

Referring back to FIG. 1, where a transparent region of the reticle 15 in which region a circuit pattern is actually formed is denoted at Q, the inspecting laser beam supplied from the laser source 10 is scanningly deflected by the mirror 11 so as to scan such range of the reticle 15 surface that is wider than the transparent pattern-bearing region Q. On the other hand, usually a reticle 15 which is used in the manufacture of semiconductor devices is coated with a thin film of a chromium material or a chromium oxide material in a region other than the region in which a circuit pattern is formed. Thus, in FIG. 1, the peripheral region R of the reticle 15 surface, surrounding the pattern bearing region Q provides a light-intercepting frame portion. The provision of such a light-intercepting frame portion of the reticle 15 surface is chiefly to prevent leakage of a photoprinting light, from the peripheral portion of the reticle, supplied from a light source (not shown) and illuminating the reticle. As seen in FIG. 2, when the reticle 15 is illuminated so that its circuit pattern formed in the pattern bearing region (the region Q) is photoprinted in a reduced scale upon different shot areas of a wafer 71 in a step-and-repeat manner by use of a reduction projection lens system 70. If there is leakage of light through the peripheral portion of the reticle 15, the leaked light from the peripheral portion of the reticle 15 sensitizes a portion of the resist material on the wafer 71 surface which portion is applied to adjacent shot areas surrounding one shot area onto which the reticle pattern is being transferred. To prevent such undesirable sensitization, the frame portion R is made non-transmissible.

Consequently, in FIG. 1, when the light beam which is emitted from the laser source and obliquely projected upon the reticle 15 through the lens 12 is incident upon the peripheral light-intercepting frame portion R, it is regularly reflected. A linear array type photoelectric detector 5a is provided at a position effective to receive the light regularly reflected from the light-intercepting frame portion R. By the provision of the detector 5a, it is now possible to determine the exact position of a foreign particle, if any, adhered to the reticle 15, as will be described below in more detail.

Figure 3:
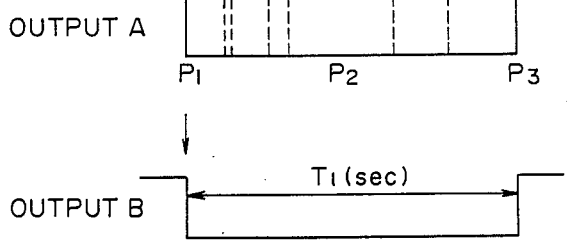
FIG. 3 is a waveform view showing an output A of a linear array type photodetector and an output B of a holding circuit, both included in the device of the first embodiment.

As the point of inspection by the scanning laser beam, being scanningly deflected by the mirror 11 and irradiating the peripheral light-intercepting frame portion R in the neighborhood of the point P0, shifts on the reticle 15 surface with the rotation or oscillation of the mirror 11 and passes the point P1 which is on the boundary between the peripheral frame portion R and the transparent pattern-bearing region Q, the scanning laser beam now passes through the transparent substrate in the region Q of the reticle 15. As a result, the output level of the photoelectric detector 5a decreases, as illustrated in FIG. 3 as an output A. In this embodiment, an electric circuit is provided which circuit is arranged to receive such an output A of the photoelectric detector 5a and to produce an output B whose level is held low for a predetermined time T1 (sec.). Within this time period, the output signals of the photodetectors 1–4 may be detected. Also, the determination of the position of a foreign particle, if any, may be executed within this time period. The holding time T1 can be preset in accordance with the wideness of the pattern bearing region Q of the reticle 15 (i.e. the interval between the points P1 and P3) and the scanning speed of the scanning laser beam upon the reticle 15 surface by the rotation or oscillation of the mirror 11. The provision of the holding circuit in this embodiment is for the following reason. That is, the reticle 15 surface within the region Q has been patterned in a specific manner in accordance with the design of the microcircuit to be manufactured. Namely, in this region Q, there are light-reflective portions and light-transmissive portions which are disposed generally in an alternating fashion. As a consequence, if the output of the photoelectric detector 5a is continuously monitored, the output level thereof changes in accordance with the circuit pattern provided on this region of the reticle 15, in the manner as depicted by broken lines in the output A of FIG. 3.

The electric arrangement of the present embodiment that provides the above-described functions is illustrated in the block diagram of FIG. 4. In this Figure, the output of the photoelectric detector 5a is amplified by an amplifier 41 whose output (output A) is applied to a comparator 42. In this comparator 42, the output A of the amplifier 41 is compared with a reference voltage Vref1. An edge trigger circuit 44 is adapted to be triggered in response to the inversion of the output signal of the comparator 42 from "high" to "low" which inversion is caused when the output A of the amplifier 41 becomes lower than the reference voltage Vref1. The edge trigger circuit 44 as it is triggered applies an output B, for the time period T1 (sec.), to each of switches 46 and 48 to thereby close them for this time period. When the switch 46 is closed, it is operable to transmit, to each of a controller 52 and a non-inversion input terminal of a comparator 49, the output signals produced by the photodetectors 1–4 (which may be arranged in the manner shown in FIG. 9 or 10 or in any other suitable manner) which are amplified by an amplifier 45. On the other hand, when the switch 48 is closed, it is operable to transmit clock pulses from a clock pulse generating circuit 47 to a counter 50. When the scanning laser beam scanningly irradiating the reticle 15 surface with the rotation or oscillation of the mirror 11 is projected upon any foreign particle or disfigurement on the reticle 15, the outputs of the photodetectors 1–4 as transmitted by way of the switch 46 become higher than a reference voltage Vref2. In response thereto, the output level of the comparator 49 is inverted from a low level to a high level. A latch 51 is operable to latch the counted number in the counter 50 at a moment of the inversion of the output level of the comparator 49, from the low level to the high level, the latched number being applied to the controller 52. Although it is not clearly illustrated in FIG. 4, the counted number in the counter 50 is continuously monitored by the controller 52, independently of the supply of the latched data from the latch 51.

In accordance with the latched data from the latch 51 and with the scanning speed (which is constant) of the scanning laser beam scanningly irradiating the reticle 15, the controller 52 determines the position of a foreign particle, if any, with respect to the point P1 which is on the boundary between the pattern bearing region Q and the light-intercepting frame portion R of the reticle 15. The thus determined position is displayed on a cathode ray tube, not shown, in an X-Y coordinate system which is preset in accordance with the reticle used. By repeating the above-described operation while moving the reticle 15 at a constant speed and in a direction perpendicular to the beam scanning direction (e.g. in a direction from S1 to S2), all the foreign particles or the like in the whole region Q as well as their positions are detected.

In accordance with the present embodiment, the outputs of the photodetectors 1–4 are processed only in a time period during which the switches 46 and 48 are closed in response to the output of the photoelectric detector 5a. Thus, while taking as a reference the boundary between the transparent pattern-bearing region Q and the light-intercepting frame portion R of the reticle 15, the position of a foreign particle, if any, and the range of inspection (i.e. from the point P1 to the point P3) can be determined or specified very accurately.

Figure 5:
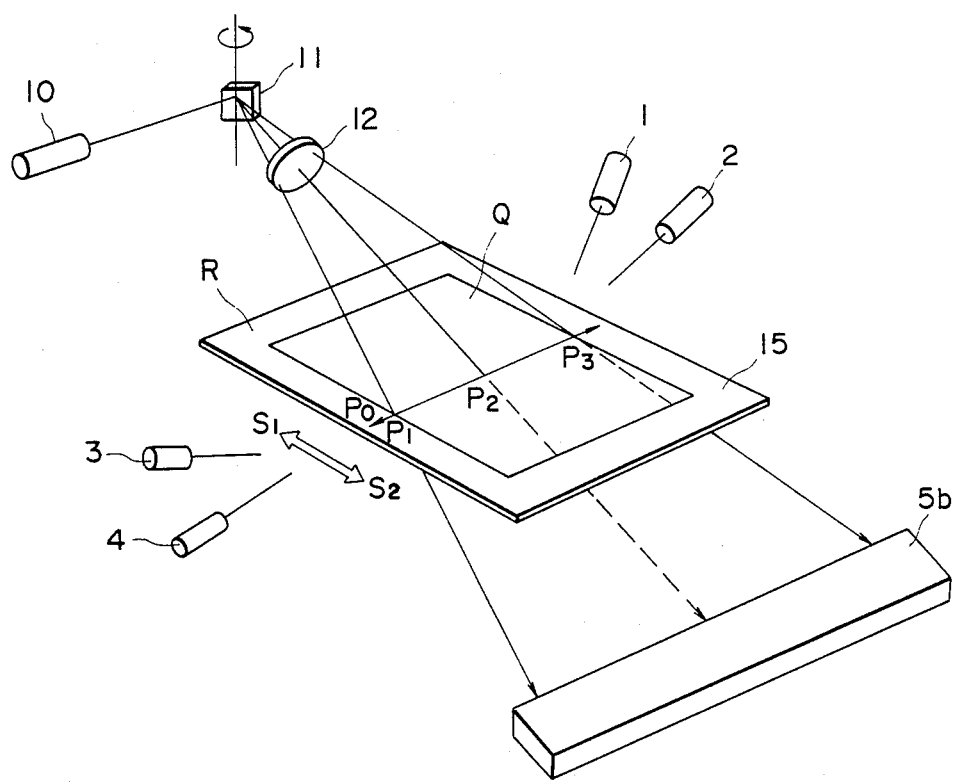
FIG. 5 is a perspective view schematically showing an optical arrangement of a surface inspecting device according to a second embodiment of the present invention.

Referring now to FIG. 5, description will be made of a surface inspecting device according to a second embodiment of the present invention. One of major distinctions of the present embodiment over the FIG. 1 embodiment resides in that a linear array type photoelectric detector 5b is disposed so as to receive the scanning laser beam from the mirror 11 and directly passed through the transparent pattern-bearing region Q of the reticle 15.

In the FIG. 1 embodiment described hereinbefore, the photoelectric detector 5a receives the scanning laser beam as being reflected by the light-intercepting frame portion R of the reticle 15 surface. Since, however, usually a reticle 15 has been patterned by use of a light-intercepting material such as chromium or chromium oxide, for example, the intensity of the reflected light changes with the reflection factor of the material used to provide the light-intercepting frame portion R. Therefore, in order to provide the output characteristics such as illustrated in FIG. 3, it is necessary to change the threshold level Vref1 (FIG. 4) for the photoelectric detector 5a each time one reticle is replaced by another. In the present embodiment shown in FIG. 5, as compared therewith, the photoelectric detector 5b is disposed so as to receive the transmitted light from the reticle 15. With this arrangement, the device is operable with a constant threshold level for different reticles, regardless of the reflection factors of these reticles.

Figure 6:
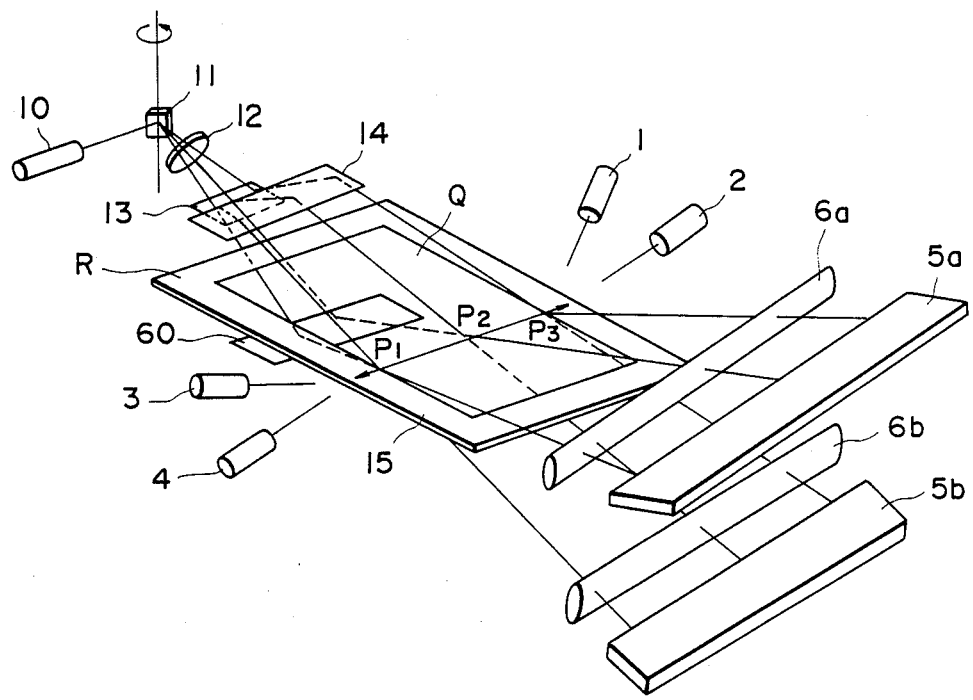
FIG. 6 is similar to FIG. 5 but shows an optical arrangement of a surface inspecting device according to a third embodiment of the present invention.

FIG. 6 shows a surface inspecting device according to a third embodiment of the present invention. In this embodiment, the invention is applied to a surface inspecting device for inspecting upper and lower surfaces of a reticle 15 in a sequential manner, such as in the case of FIG. 9 described hereinbefore. While, in the present embodiment, two linear array type photoelectric detectors 5a and 5b are used for the detection of the boundary P1 on the reticle 15 surface, one of them may be omitted. For example, where only the upper photoelectric detector 5a is provided, it is used to detect the light reflected from the light-intercepting frame portion R of the reticle 15 for the inspection of the upper surface of the reticle 15 (i.e. at the time when the mirror 13 is inserted into the optical path from the mirror 11). Also, this detector 5a is used to detect the light passed through the transparent pattern-bearing region Q of the reticle 15 for the inspection of the lower surface of the reticle 15 (i.e. in a case wherein the mirror 13 is retracted from the optical path). On the other hand, when both photoelectric detectors 5a and 5b are provided, they can be used to detect only the light as passed through the transparent region Q for the inspection of the upper and lower surfaces of the reticle. Thus, in such case, the advantageous effects as having been described with reference to the FIG. 5 embodiment are attainable.

In the present embodiment shown in FIG. 6, additionally there are provided lenses 6a and 6b each disposed in front of an associated one of the photoelectric detectors 5a and 5b. The scanning laser beam from the mirror 11 is usually concentrated upon the reticle 15 surface. As a consequence, on the light-receiving surface of each photoelectric detector 5a or 5b, the light reflected from or passed through the reticle 15 is diverged at least to some degree. In consideration of this, the lenses 6a and 6b are provided. Each of these lenses 6a and 6b comprises a cylindrical lens having a generating line extending substantially in parallel to the scan direction defined by the scanning laser beam scanningly deflected by the mirror 11. Thus, each of the lenses 6a and 6b has a function of concentrating the light, reflected from or passed through the reticle 15, upon the light-receiving surface of the photoelectric detector 5a or 5b. With this arrangement, the intensity of the light upon the light-receiving surface of the photoelectric detector can be increased with the result that the signal-to-noise ratio of the boundary detecting signal can be improved significantly.

Figure 7:
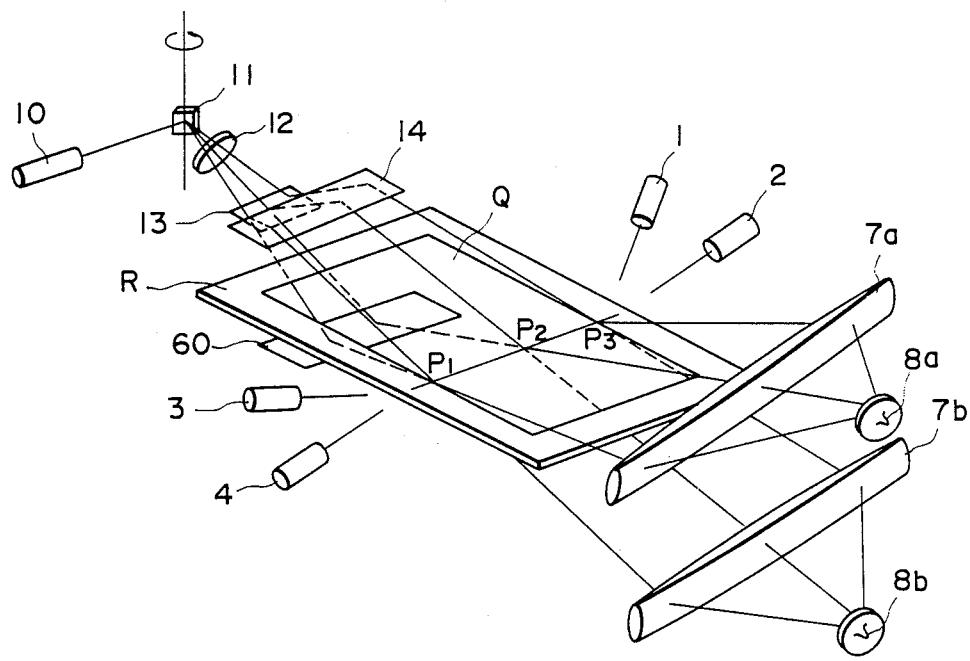
FIG. 7 is a view similar to FIG. 5 but shows an optical arrangement of a surface inspecting device according to a fourth embodiment of the present invention.

FIG. 7 shows a surface inspecting device according to a fourth embodiment of the present invention. One of important features of the present embodiment resides in that spherical lenses 7a and 7b are provided in front of photoelectric detectors 8a and 8b, respectively. Another important feature resides in that each of the photoelectric detectors 8a and 8b is disposed in a plane which is optically conjugate with the scanning mirror 11. In this optically conjugate plane, the light directly reflected from or passed through the reticle 15 is always converged into a spot having a certain spot size, independently of the degree of deflection (scan) of the laser beam by the mirror 11. Accordingly, each photoelectric detector 8a or 8b may be of a type other than the linear array type. Thus, a compact detector is attainable.

Figure 8:
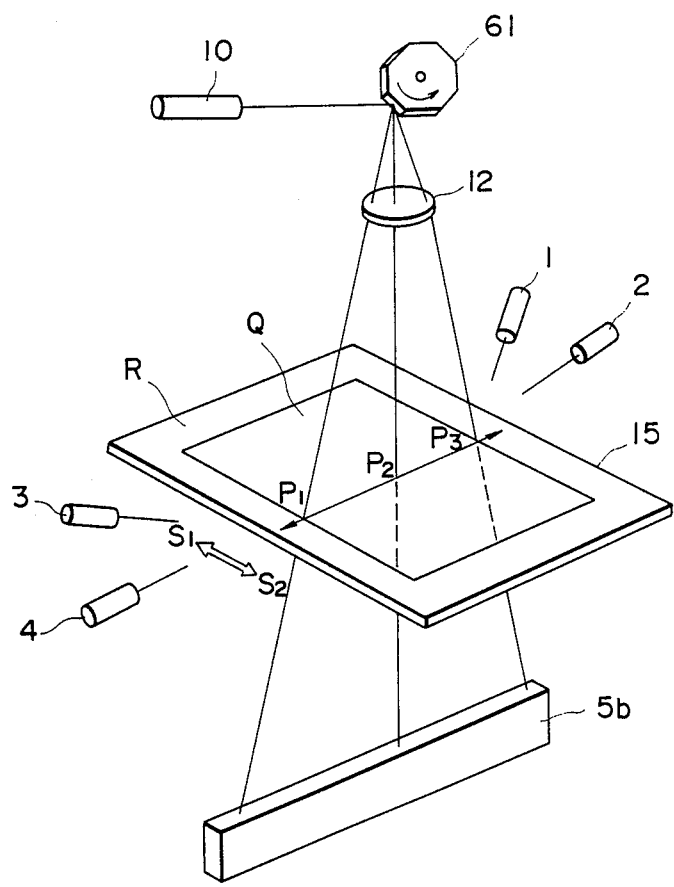
FIG. 8 is a view similar to FIG. 5 but showing an optical arrangement of a surface inspecting device according to a fifth embodiment of the present invention.

FIG. 8 shows a surface inspecting device according to a fifth embodiment of the present invention. A major distinctive feature of the present embodiment over the FIG. 5 embodiment resides in that the laser beam from the laser 10 is scanningly deflected by a rotatable polygonal mirror 61 so that the scanning laser beam is projected upon the reticle 15 surface substantially along a plane perpendicular to the reticle 15 surface. In this case also, the advantageous effects of the present invention having been described hereinbefore are obtainable.

While, in the foregoing, the invention has been described chiefly with reference to the inspection of the presence/absence of dust or foreign particles adhered to the surface of a reticle, the present invention is not limited to the disclosed embodiments but is applicable also to any other type inspection of a surface of an article, such as, for example, the inspection of any defect or disfigurement of a patterned surface of a plate-like or sheet like article preferably having a reflective frame surface portion.

In accordance with the preferred embodiments of the present invention, as has hitherto been described, the position of the boundary between a transparent effective region of a substrate such as a reticle and a peripheral light-intercepting frame portion of the substrate is determined on the basis of the detection of a rapid change in the quantity of light (scanning light) as reflected from or passed through a portion of the substrate in the neighborhood of the boundary. By using the thus determined position of the boundary as a reference, the position of a foreign particle or the like, is determined or detected. Therefore, when the present invention is used for the inspection of a reticle having a circuit pattern prepared for the manufacture of microcircuits, the position of such a foreign particle even if it is on the circuit pattern of the reticle can be measured very accurately, and also, automatically. As a result, it is possible to discriminate unfavorableness of the adhered particle. For example, it is possible to discriminate whether the adhered particle is on a light-intercepting material of the circuit pattern. Therefore, the frequency of cleaning the reticle can be reduced. Also, by this reduction, unnecessary processes may be omitted with the result that the throughput in the semiconductor device manufacturing processes can be improved significantly.

While the invention has been described with reference to the structures disclosed herein, it is not confined to the details set forth and this application is intended to cover such modifications or changes as may come within the purposes of the improvements or the scope of the following claims.

What is claimed is:

1. A device for inspecting the state of the surface of a reticle having a patterned portion formed with a pattern thereon and a light-intercepting portion formed around the patterned portion, said device comprising:
   a light source for producing a light beam;
   scanning means for scanning the reticle with the light beam produced by said light source;
   detecting means for detecting the boundary between the patterned portion and the light-intercepting portion of the reticle by use of the light beam caused to scan the reticle by said scanning means; and
   inspecting means for inspecting the state of the surface of the reticle, by use of the light beam caused to scan the reticle by said scanning means, for a predetermined time period after the boundary between the patterned portion and the light-intercepting portion is detected by said detecting means.

2. A device according to claim 1, wherein said detecting means includes a detector for detecting the light beam from the article.

3. A device for inspecting the state of the surface of a reticle having a patterned portion formed with a pattern thereon and a light-intercepting portion formed around the patterned portion, said device comprising:
   a light source for producing a light beam;
   scanning means for scanning the reticle with the light beam;
   detecting means for detecting the boundary between the patterned portion and the light-intercepting portion of the reticle by use of the light beam causes to scan the reticle by said scanning means, said detecting means producing an inspection start signal in response to the detection of the boundary;
   pulse producing means for producing clock pulses;
   counting means for counting the clock pulses produced by said pulse producing means;
   operating means enabled in response to the inspection start signal to cause said counting means to start counting of the clock pulses;
   inspecting means for inspecting the state of the surface of the reticle, by use of the light beam caused to scan the reticle by said scanning means, for a predetermined time period after the inspection start signal is produced; and
   discriminating means for discriminating the state of the surface at each position on the reticle, on the basis of the detection by said detecting means and the number of clock pulses counted by said counting means.

4. A device according to claim 3, wherein said detecting means detects the light beam as passed through the article.

* * * * *

UNITED STATES PATENT AND TRADEMARK OFFICE
CERTIFICATE OF CORRECTION

PATENT NO. : 4,831,274

DATED : May 16, 1989

INVENTOR(S) : Michio Kohno, et al

It is certified that error appears in the above-identified patent and that said Letters Patent is hereby corrected as shown below:

Column 3

Line 16, "drawings" should read --drawings.--.

Column 4

Line 34, "detected" should read --detected.--.
   Line 39, "elements 66-18" should read --elements 16-18--.

Column 6

LIne 55, "clearly" should be deleted.

Column 10

Line 18, "causes" should read --caused--.

Signed and Sealed this

Second Day of February, 1993

*Attest:*

STEPHEN G. KUNIN

*Attesting Officer*     *Acting Commissioner of Patents and Trademarks*